ns
| [19] | [11] | Patent Number: | 5,813,402 |
| [45] | Date of Patent: | Sep. 29, 1998 |

United States Patent
Jinotti

[54] VALVE FOR PULMONARY CATHETER

[76] Inventor: Walter J. Jinotti, 10 Scott St., New Brunswick, N.J. 08903

[21] Appl. No.: 831,654

[22] Filed: Apr. 9, 1997

[51] Int. Cl.$^6$ .................................................. A61M 16/00
[52] U.S. Cl. ............................ 128/207.16; 128/205.24; 128/912
[58] Field of Search .............................. 128/207.16, 912, 128/205.24, DIG. 26

[56] References Cited

U.S. PATENT DOCUMENTS

| 4,036,210 | 7/1977 | Campbell et al. | 128/207.16 |
| 4,202,330 | 5/1980 | Jariabka | 128/207.16 |
| 4,595,005 | 6/1986 | Jinotti | 128/207.16 |
| 4,649,914 | 3/1987 | Kowalewski | 128/207.16 |
| 4,850,350 | 7/1989 | Jackson | 128/207.16 |
| 4,995,387 | 2/1991 | Jinotti | 128/912 |
| 5,088,486 | 2/1992 | Jinotti | 128/912 |
| 5,191,881 | 3/1993 | Beck | 128/207.16 |
| 5,255,672 | 10/1993 | Jinotti | 128/207.16 |
| 5,487,381 | 1/1996 | Jinotti | 128/207.16 |
| 5,511,545 | 4/1996 | Jinotti | 128/207.16 |
| 5,611,336 | 3/1997 | Page et al. | 128/207.16 |

*Primary Examiner*—Aaron J. Lewis
*Attorney, Agent, or Firm*—Robert A. Green

[57] ABSTRACT

The disclosure is of apparatus for transporting treatment means to a pulmonary patient and including sealing means embedded in parts thereof to prevent leakage of the treatment means.

11 Claims, 5 Drawing Sheets

VALVE FOR PULMONARY CATHETER

BACKGROUND OF THE INVENTION

The present invention relates to pulmonary catheters for use in providing suction or oxygen or medication in connection with the treatment of pulmonary patients. The present inventor has created various forms of apparatus of this type and they operate well. However, under some circumstances, it is desirable that pulmonary catheters and associated control valves be capable of operating under considerable pressure without leaking.

U.S. Pat. No. 4,193,406 of the present inventor describes and claims one type of control valve usable in treating pulmonary patients and this valve is described and claimed herein along with new and inventive improvements which improve its operation. Another type of control valve which embodies the present invention is described and claimed in U.S. Pat. No. 5,140,983 of the present inventor which is incorporated herein by reference.

While the valves shown in the aforementioned patents operate well, under some circumstances of oxygen or suction feed, leakage may occur in the valves and this may be undesirable. The present invention solves this problem and provides a pulmonary control valve which can provide suction or oxygen or medication under relatively high pressure without leaking.

SUMMARY OF THE INVENTION

A pulmonary control valve embodying the invention includes portions which move with respect to each other to permit oxygen or suction or medication to flow through apertures therein and means is provided around the apertures to prevent the flowing substance from leaking therefrom.

DETAILED DESCRIPTION OF THE INVENTION

Figure 1:
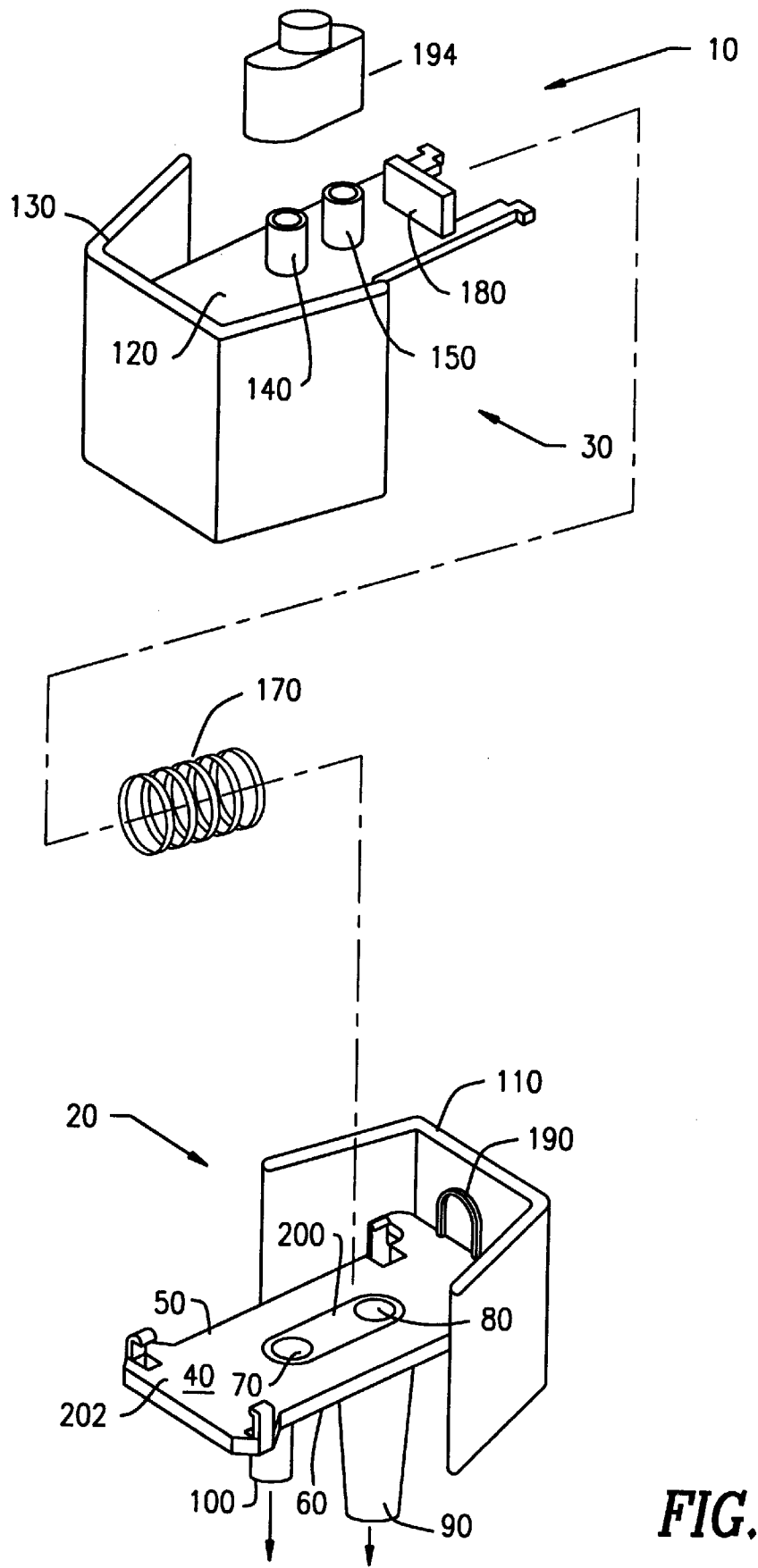
FIG. 1 is an exploded view of apparatus embodying the invention.

The following patents of the subject inventor are incorporated herein by reference: U.S. Pat. Nos. 4,595,005; 4,995,387; 5,088,486; 5,140,983; 5,255,672; and 5,346,478

One embodiment of the invention is shown in FIGS. 1 to 4 which show a pulmonary valve 10 for providing oxygen or suction or other treatment to a patient. The valve includes two portions 20 and 30 which are coupled together so that they slide with respect to each other to connect different possible treatment sources selectively to a patient.

The lower portion 20 of valve 10 includes a flat plate 40 which has a top surface 50 and a bottom surface 60, a first bole 70 which is a suction hole, and a second hole 80 which is an oxygen hole, in one mode of operation thereof. The oxygen hole 80 communicates with a tube 90 which extends downwardly from the lower surface of the plate 40 and is coupled to a source of oxygen and the suction hole communicates with a tube 100 which extends downwardly from the lower surface of the plate 40 and is coupled to a source of suction. The tubes 90 and 100 may be connected to sources of other materials if desired. The external tubes may be of different sizes or shaped differently to permit foolproof and easy coupling of other tubing thereto.

A U-shaped frame portion 100 is secured to the plate 40 to form a housing for the valve 10.

The upper portion of the valve 30 similarly includes a flat plate 120 to which is secured a U-shaped frame portion 130 which meshes with the lower frame portion 110 to complete the housing for the valve 10.

The upper flat plate carries two short pipes or tubes 140 and 150 which extend through the plate. In the assembled valve, the pipe 140 is aligned with the hole 70 in plate 40 and the pipe 150 is aligned with the hole 80 in the bottom plate 40.

The plates 40 and 120 are held together by guide hooks 160 which permit them to slide with respect to each other and a helical spring 170 is disposed between a bumper 180 on the top surface of the upper plate 120 and a guide 190 on the wall of the upper frame member 130 to hold the spring in place. The spring normally urges the top plate to the left as seen in FIG. 1.

A cap 194 is secured to the short tubes or pipes 140 and 150 to couple the two pipes by a single tube to a patient.

Figure 4:
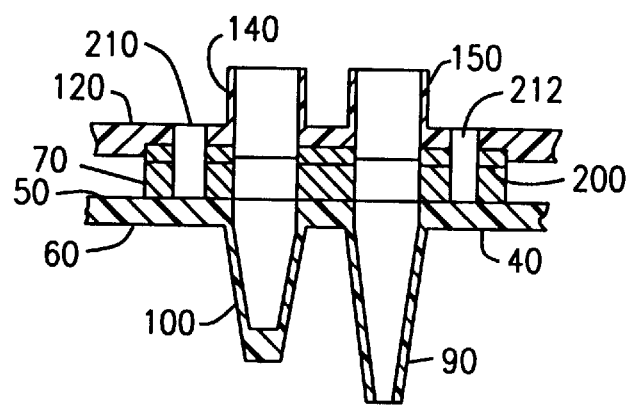
FIG. 4 is a sectional view along a portion of the line 4—4 in FIG. 2.
Figure 5:
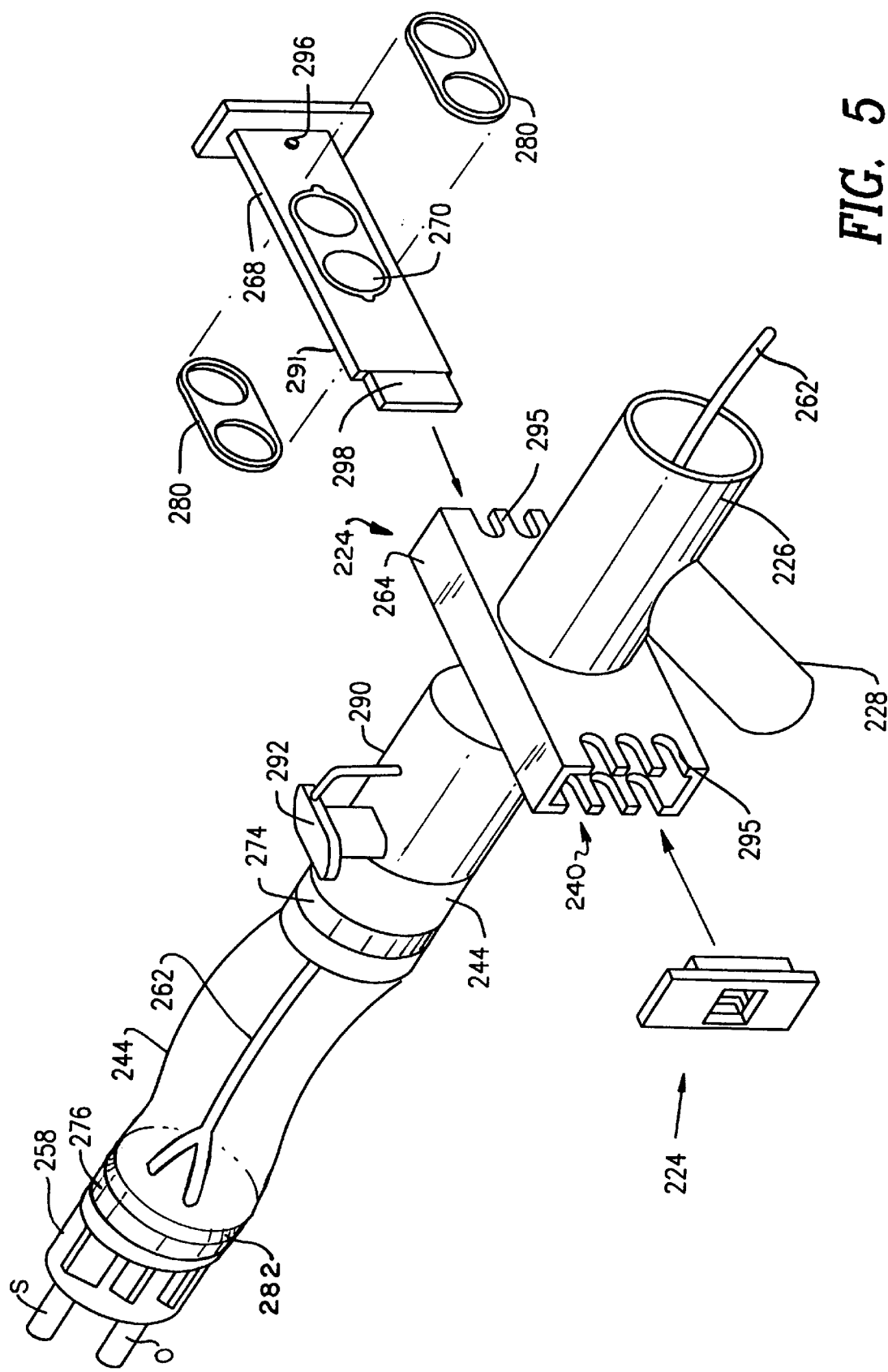
FIG. 5 is a perspective view, partly exploded, of a modification of the invention.
Figure 6:
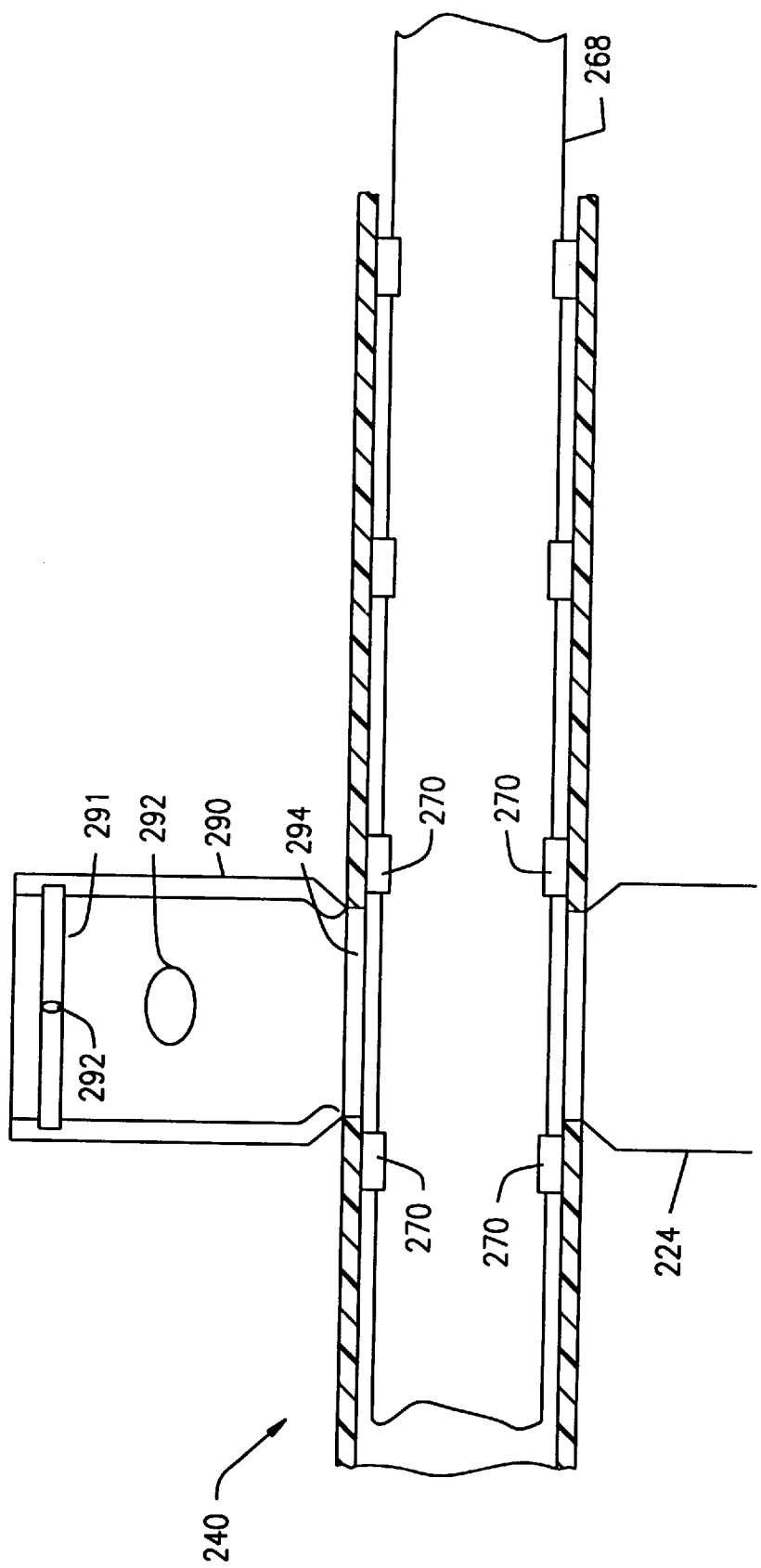
FIG. 6 is a side elevational view of the apparatus of FIG. 5.
Figure 8:
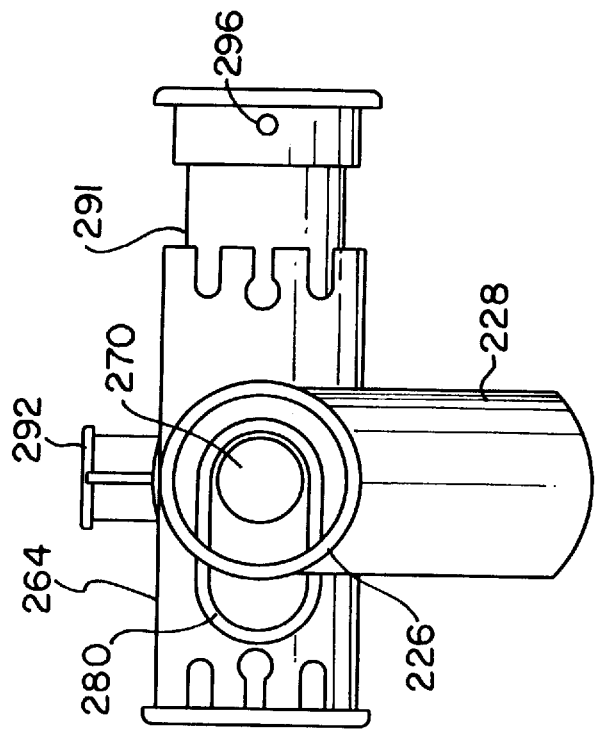
FIG. 8 is a sectional view of a portion of the apparatus of FIG. 5.
Figure 7:
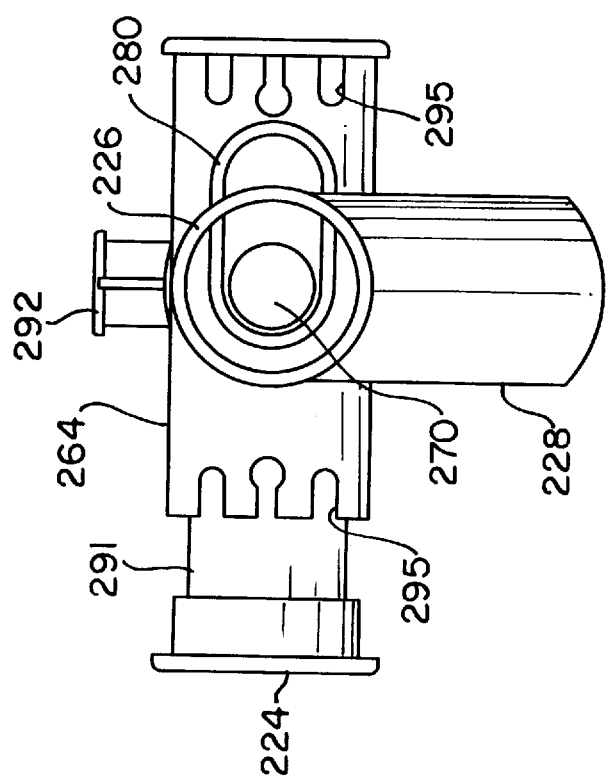
FIG. 7 is an opposite side elevational view of the apparatus of FIG. 5.

According to the invention, in order to provide a tight fit of all parts and to prevent leakage from the holes in the bottom plate, a two-part O-ring or spacer 200 is secured to the top surface of bottom plate 40. The O-ring has portions closely surrounding the holes in the plate as shown in FIGS. 1 and 4. The ring 200 is of a relatively rigid, rubber-like, flexible material and it is embedded in the top surface of the plate 40. The ring is in fluid-tight contact with the surface 50 and prevents leakage of suction or oxygen or other substance along the top surface of the plate 40 from the holes. If desired or necessary a similar ring or spacer 202 may be positioned along the periphery of the top surface of the plate 40 between the two plates 40 and 120. The plates 20 and 120 slide along the O-rings or spacers in liquid tight engagement therewith.

Figure 3:
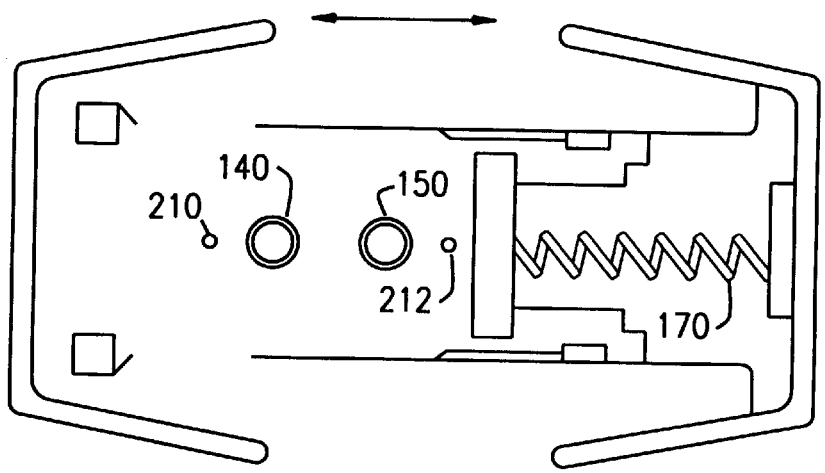
FIG. 3 is a plan view of the apparatus of FIG. 2 at another stage in its operation.

In one mode of operation of the valve 10, a source of oxygen is connected to tube 90 and a source of suction is connected to tube 70. These sources are not shown. The valve 10 is first expanded by the spring 170 as seen in FIG. 3 and the two plates and associated structure thereof are moved with respect to each other to a first position. In this orientation of the parts, the oxygen source is coupled through tube 150 and the cap 194 to a patient.

As noted above, the O-ring 200 prevents any leakage of the oxygen around the holes 70 and 80.

Figure 2:
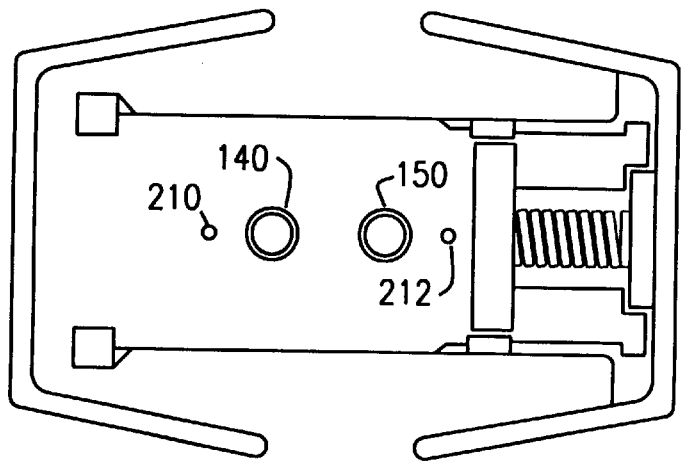
FIG. 2 is a plan view of the apparatus of FIG. 1 at one stage in its operation.

The holes 210 and 212 shown in FIGS. 2 and 3 vent to atmosphere alternately.

When desired, the operator presses the two parts of the valve together against the spring 170 and the hole 70 carrying suction is fed through tube 140 and the outlet tube in the cap 194 to the patient. Again, the O-ring 200 prevents the suction from leaking around the hole 70.

Another pulmonary-use valve 220 embodying the principles of the invention is shown in FIGS. 5–8. This valve includes a mouthpiece 224 having a first tubular portion 226 which is placed in a patient's mouth and a second tubular portion 228 extending therefrom which is connected to a source of oxygen (not shown). The mouthpiece extends rearwardly through a sliding valve or door mechanism 240 to a third tubular portion 290.

A cleanout valve 292 is provided in tube 290. A cleaning fluid can be introduced through valve 292 to wash out the tube 290 and the end of the catheter held therein. If desired, a sponge or other cleaning means can be placed in tube 290 as described in U.S. Pat. No. 5,088,486.

According to the invention, a relatively rigid, thin disk 291 is secured in place, in any suitable fashion, in the open end of tube 290 to effectively seal off this end of tube 290. The opposite end of tube 290 is sealed off when desired by apparatus to be described. The disk 291 has a slit 293 through which a catheter can be fed into the mouthpiece and into a patient.

The third tubular portion 290 may be coupled to apparatus of the type shown in Jinotti U.S. Pat. No. 5,140,983. Thus, the third tube is releasably connected to one end of a collapsible sleeve 244 by means of a locking ring 274 and the other end is releasably connected to an adapter 276 by a locking ring 280. The adapter is coupled to the valve 258. An arrangement of this type is shown in U.S. Pat. No. 5,346,478 and in U.S. Pat. No. 5,346,478. Valve 258 is coupled to sources of oxygen and suction for application to a patient under the control of the valve.

A dual or single lumen catheter 262 is coupled to the adapter 276 and it is adapted to be inserted through the mouthpiece into a patient by an operator grasping the valve 258 and all of the associated apparatus.

According to the invention, between the first tube and the third tube is the sliding door apparatus 240 for controlling the access of the catheter 262. The third tube 290 carries disk 291 which has a slit 292 through which the catheter can pass and the passage is controlled by a box-like structure 264 secured between the tube 290 and the tube 224. The box has a hole 294 aligned with the opening in the adjacent open end of tube 290. A slidable plate 268 is slidably disposed within the box 264 and it has a hole 270 which is adapted, in one position of plate 268, to be aligned with the hole in the box and tube 290 and, in another position it blocks the holes in the box and the tube 290. This latter position is assumed after the catheter is withdrawn from a patient into the tube 290 where it can be cleaned as described in U.S. Pat. No. 5,088,486.

In one arrangement, both ends of the box 264 are provided with notches 295 into which pins 296 and 298 carried at both ends of the slidable plate 268 are adapted to seat in the notches 295 to hold the slidable polate securely in place.

Under some circumstances, as the flow of oxygen or suction takes place through the mouthpiece, there might be leakage between the box 264 and the slidable plate 268. Although this leakage may or may not be undesirable, it is prevented according to the invention by the provision of sealing members 280, like the seal 200 in FIG. 1. The sealing members are of a relatively rigid, rubber-like material and they are slightly embedded in the opposed surfaces of the slidable plate 268. The sealing members include O-ring portions one of which surrounds the opening in the plate and are in fluid-tight engagemen with the surfaces of the box 264 and prevent leakage from this opening.

In operation of the mouthpiece and the associated apparatus, the slidable plate 268 is moved to the position in which the opening 270 therein is aligned with the opening in tube 290 and the catheter assembly is pushed forward to cause the catheter to pass through the mouthpiece into the patient. Oxygen and suction are applied as described in the above patents and thereafter the catheter is pulled back through the slidable plate into the tube 290 but in front of the disk 291. The slidable plate is moved to the right as seen in FIG. 1 to seat a solid portion of the plate in front of the hole in the end of tube 290 to thereby block the hole and to provide a closed chamber in which the end of the catheter is seated. The catheter end may now be washed by means of fluid introduced through valve 292 and the washing fluid may be removed by means of suction applied from valve 258.

As can be seen, all parts of the apparatus of the invention can be disassembled and discarded or some parts may be re-used on the same patient. It is noted that the sleeve 244 encloses the catheter and protects an operator from any material which may be thereon. The assembly of catheter and sleeve can be discarded.

What is claimed is:

1. A pulmonary valve apparatus for providing medication to a patient including
    a generally tubular body providing a flow path from a source of medication to a patient,
        said tubular body having a first end adapted to be coupled to various forms of medication and a second end adapted to be coupled to a patient for receiving said medication,
    a slide means disposed within a slide path in said tubular body for selectively closing and opening said flow path through said tubular body, and
    sealing means disposed between said slide means and said slide path for insuring a tight seal between said slide means and said slide path; a valve coupled to said rear portion of said tubular body, a source of suction and a source of oxygen coupled to said valve, said valve being operable to connect either suction or oxygen to said tubular body and thus to a patient.

2. The apparatus defined in claim 1 wherein said slide path comprises a channel disposed transverse to said flow path in said tubular body.

3. The apparatus defined in claim 2 wherein said channel divides said tubular body into a front portion and a rear portion.

4. The apparatus defined in claim 3 wherein said tubular body has a wall and said wall of said rear portion of said tubular body has an inlet for introducing cleaning solutions into said front portion of said tubular body.

5. The apparatus defined in claim 1 wherein said slide means is slidably disposed in said slide path channel, said slide means including a hole which can be disposed in or out of communication with said flow path depending on the position of said slide means in said channel.

6. The apparatus defined in claim 5 wherein said slide means comprises a generally flat plate having and aperture therein, said sealing means surrounding said aperture.

7. The apparatus defined in claim 1 wherein said sealing means is of a flexible, deformable material.

8. The apparatus defined in claim 1 wherein said sealing means surrounds said flow path.

9. The apparatus defined in claim 1 and including a flexible catheter tube coupled from said valve and through said tubular body to a patient.

10. The apparatus defined in claim 9 and including a flexible protective sheath enclosing said catheter tube and extending from said valve to said rear portion of said tubular body, said flexible protective sheath and said catheter both being removable and discardable.

11. The apparatus defined in claim 1 and including said valve having a first inlet means for coupling a source of suction thereto and second inlet means for coupling a source of oxygen or other patient treating material thereto, said valve having vent means for alternately coupling oxygen or suction to atmosphere.

* * * * *